(12) United States Patent
Zerbe et al.

(10) Patent No.: US 9,301,948 B2
(45) Date of Patent: Apr. 5, 2016

(54) INSTANTLY WETTABLE ORAL FILM DOSAGE FORM WITHOUT SURFACTANT OR POLYALCOHOL

(71) Applicant: IntelGenx Corp., St.-Laurent, Quebec (CA)

(72) Inventors: Horst G. Zerbe, Quebec (CA); Angela Angusti, Montreal (CA); Nadine Paiement, St.-Laurent (CA)

(73) Assignee: IntelGenx Corp., St.-Laurent (CA)

( * ) Notice: Subject to any disclaimer, the term of this patent is extended or adjusted under 35 U.S.C. 154(b) by 0 days.

(21) Appl. No.: 14/447,071

(22) Filed: Jul. 30, 2014

(65) Prior Publication Data

US 2015/0038540 A1    Feb. 5, 2015

Related U.S. Application Data

(60) Provisional application No. 61/860,345, filed on Jul. 31, 2013.

(51) Int. Cl.

| | |
|---|---|
| *A61K 31/4196* | (2006.01) |
| *A61K 47/02* | (2006.01) |
| *A61K 47/32* | (2006.01) |
| *A61K 47/38* | (2006.01) |
| *A61K 9/00* | (2006.01) |
| *A61K 31/422* | (2006.01) |
| *A61K 31/473* | (2006.01) |
| *A61K 31/5513* | (2006.01) |
| *A61K 31/5517* | (2006.01) |

(52) U.S. Cl.
CPC ............. *A61K 31/4196* (2013.01); *A61K 9/006* (2013.01); *A61K 31/422* (2013.01); *A61K 31/473* (2013.01); *A61K 31/5513* (2013.01); *A61K 31/5517* (2013.01); *A61K 47/02* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,709,671 B2 | 3/2004 | Zerbe et al. | |
| 2005/0118217 A1 | 6/2005 | Barnhart et al. | |
| 2010/0112050 A1* | 5/2010 | Ryoo | A61K 9/0056 424/465 |
| 2010/0285130 A1* | 11/2010 | Sanghvi | A61K 9/006 424/484 |
| 2011/0136815 A1 | 6/2011 | Zerbe et al. | |

FOREIGN PATENT DOCUMENTS

CA    2704079 A1    6/2009

OTHER PUBLICATIONS

International Search Report dated Feb. 25, 2015, Form PCT/ISA/220, 8 pages.

* cited by examiner

*Primary Examiner* — Bethany Barham
*Assistant Examiner* — Barbara Frazier
(74) *Attorney, Agent, or Firm* — Butzel Long

(57) ABSTRACT

An instantly wettable and rapidly disintegrating oral film dosage form without a surfactant and without a polyalcohol was achieved by combining at least one water soluble polymer that is not a copolymer of vinylpyrrolidone, at least one active agent, a copolymer of vinylpyrrolidone and titanium dioxide. In certain embodiments, the film comprises hydroxypropyl cellulose or a combination of hydroxypropyl cellulose and a polymer or copolymer of vinylpyrrolidone or a substituted vinylpyrrolidone as the water soluble polymer(s). A plasticizer, and optional additives selected from synthetic sweeteners, natural sweeteners, flavorants, antioxidants, colorants, and opacifiers, can be added to the disclosed film oral dosage forms.

20 Claims, No Drawings

INSTANTLY WETTABLE ORAL FILM DOSAGE FORM WITHOUT SURFACTANT OR POLYALCOHOL

CROSS-REFERENCE TO RELATED APPLICATIONS

This application claims the benefit of U.S. Provisional Application No. 61/860,345, filed Jul. 31, 2013, which is incorporated herein by reference.

FIELD OF THE DISCLOSURE

This disclosure relates to rapidly disintegrating films for oral administration of an active agent, and more particularly to films of this type that exhibit instant wettability and excellent mouth feel due to the absence of noticeable particulate residues.

BACKGROUND OF THE DISCLOSURE

Film type oral dosage forms are often preferred by subjects that have difficulty swallowing a tablet. However, it is important that the film dissolves or disintegrates very rapidly without leaving a gritty residue. Thus, developing a film type oral dosage form that can achieve instant wettability and rapid disintegration, while exhibiting good mouth feel is desirable. This disclosure relates to rapidly disintegrating films for oral administration of an active agent, and more particularly to films of this type that exhibit instant wettability and excellent mouth feel due to the absence of noticeable particulate residues.

SUMMARY OF THE DISCLOSURE

It has been discovered that film oral dosage forms achieving instant wettability and rapid disintegration upon oral administration can be achieved without a surfactant and without a polyalcohol. Specifically, it has been determined that at least one water soluble polymer that is not a copolymer of vinylpyrrolidone can be combined with one or more active agents, a copolymer of vinylpyrrolidone, and titanium dioxide to provide an instantly wettable, rapidly disintegratable film dosage form exhibiting good mouth feel and that is free of surfactants and polyalcohols.

A desirable combination of strength, stiffness, and disintegratability can be achieved by adding the copolymer of vinylpyrrolidone and titanium dioxide in a ratio by weight of from 3:1 to 5:1.

Also disclosed are particular embodiments in which desirable properties are enhanced by the addition of a food grade or pharmaceutically safe plasticizer.

These and other features, advantages and objects of the various embodiments will be better understood with reference to the following specification and claims.

DETAILED DESCRIPTION OF THE DISCLOSURE

The term "instantly wettable" and variations thereof generally refers to the ability of the film dosage form to rapidly imbibe moisture upon oral administration to a subject and immediately soften, whereby the subject is prevented from experiencing a prolonged adverse feeling in the mouth, and with respect to certain aspects of the disclosure refers to embodiments in which moisture (i.e., water) applied to a surface of the film penetrates the thickness of the film (e.g., typically about 5 μm to 200 μm) within 5, 10 or 15 seconds.

The term "rapidly disintegrating" and variations thereof generally refers to the ability of the film dosage forms to break up into submicron particles or completely dissolve within an acceptable period of time (e.g., within 60 seconds, within 45 seconds, within 30 seconds, within 20 seconds, or within 15 seconds of being administered, i.e., placed in the oral cavity of a subject).

The term "good mouth feel" generally refers to a variety of perceived qualities relating to texture and consistency, and most notably within the context of this disclosure to graininess (i.e., the extent to which the films can be perceived to contain grainy particles), and to the overall subjective perception of the subject to which the film is orally administered.

Water soluble polymers that are not a copolymer of vinylpyrrolidone that can be employed in the disclosed films include water soluble cellulose derivatives, including hydroxypropylmethyl cellulose, hydroxyethyl cellulose, hydroxypropyl cellulose; polyvinyl pyrrolidone (PVP); polymers of substituted vinylpyrrolidone; derivatives of polyvinyl pyrrolidone; polyethylene oxide, carboxymethyl cellulose; polyvinyl alcohol; natural gums, including xanthan, tragacanth, guar, acacia and arabic gums; and water soluble polyacrylates. Combinations of these water soluble polymers or other water soluble polymers can also be used. Examples of substituted vinyl pyrrolidones include N-vinyl-3-methyl-2-pyrrolidone, N-vinyl-4-methyl-2-pyrrolidone, N-vinyl-5-methyl-2-pyrrolidone, N-vinyl-5,5-dimethyl-2-pyrrolidone, N-vinyl-3,3,5-trimethyl-2-pyrrolidone and others.

The term "active agent" refers to any agent that is being administered orally to a subject and includes pharmaceutically active agents, nutraceutically active agents, and breath freshening agents. Examples of pharmaceutically active agents include ACE-inhibitors, antianginal drugs, anti-arrhythmics, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, tadalafil, and vardenafil, fertility agents, gastrointestinal agents, homeopathic remedies, hormones, hypercalcemia and hypocalcemia management agents, immunomodulators, immunosuppressives, anti-migraine preparations such as rizatriptan, eletriptan and zolmitriptan, motion sickness treatments, muscle relaxants, obesity management agents, osteoporosis preparations, oxytocics, parasympatholytics, parasympathomimetics, prostaglandins, psychotherapeutic agents, respiratory agents, sedatives such as lorazepam or diazepam, smoking cessation aids such as bromocryptine or nicotine, sympatholytics, tremor preparations, urinary tract agents, vasodilators, laxatives, antacids, ion exchange resins, antipyretics, appetite suppressants, expectorants, anti-anxiety agents such as alprazolam, anti-ulcer agents, anti-inflammatory substances, coronary dilators, cerebral dilators, peripheral vasodilators, psycho-tropics, stimulants, anti-hypertensive drugs, vasoconstrictors, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spadmodics, terine relaxants, anti-obesity drugs, erythropoietic drugs, anti-astmatics, cough suppressants, mucolytics, DNA and genetic modifying drugs, and combinations thereof. Examples of nutraceutically active agents include various dietary supplements, vitamins, minerals, herbs and nutrients. Breath freshening agents include, for example, spearmint oil, cinnamon oil, peppermint oil, clove oil, menthol, etc.

The film oral dosage forms disclosed herein are free or substantially free of surfactants and polyalcohols. The term "substantially free" of surfactants and polyalcohols means that the film oral dosage forms contain no deliberately added surfactants or polyalcohols, and any unavoidable or incidental surfactants or polyalcohols are only present, if at all, as impurities in other ingredients in amounts that do not affect measurable properties relating to wettability (e.g., contact angle goniometer measurements), dissolution or disintegration rates by more than 10%, and do not adversely affect measurable stability properties. The term "free" of surfactants and polyalcohols means that incidental or unavoidable surfactants and polyalcohol impurities are present in only inconsequential amounts that affect water contact angle measurements and dissolution rate by less than 1%. In certain embodiments, the presence of surfactants and polyalcohols are each limited to less than 1000 ppm (w/w), less than 500 ppm (w/w), less than 100 ppm (w/w), less than 40 ppm (w/w), or less than 10 ppm (w/w).

The terms "surfactant" and "polyalcohol" are intended to have their ordinary meanings. Specifically, the term "surfactant" is intended to mean an amphophilic compound that lowers the surface tension of a liquid, the interfacial tension between two liquids, or the interfacial tension between a liquid and a solid. The term "polyalcohol" means a sugar alcohol, which is a hydrogenated form of a carbohydrate having a carbonyl group that has been reduced to a primary or secondary hydroxyl group. Polyalcohols are also distinguishable based on their chemical formula. Polyalcohols have the general formula $H(HCHO)_{n+1}H$, whereas sugars have the general formula $H(HCHO)_n$ HCO. Common examples of polyalcohols or sugar alcohols that are avoided or eliminated from the disclosed films include glycol, glycerol, erythritol, threitol, arabitol, xylitol, ribitol, mannitol, sorbitol, galactitol, fucitol, iditol, inositol, volemitol, isomalt, maltitol, lactitol, maltotritol and maltotetraitol.

The copolymer of vinylpyrrolidone can be generally any copolymer of vinylpyrrolidone. Commerically available vinylpyrrolidone-vinyl acetate copolymers (copovidones) that may be used in the films described herein include Kollidon® VA 64 copovidone, Kollidon® 25 copovidone, Kollidone® SR copovidone, and Plasdone® S-630 copovidone. The addition of copovidone increases the stiffness of the film, e.g., increasing flexural modulus, tensile strength, and hardness. Other examples of vinylpyrrolidone copolymers that could be used include poly (1-vinylpyrrolidone-co-2-dimethylaminoethyl methacrylate, poly (1-vinylpyrrolidone-co-styrene), poly (1-vinylpyrrolidone)-graft-(1-triacontene), poly (vinylpyrrolidone-co-methyl methacrylate), poly (vinylpyrrolidone-co-N,N'-dimethylacrylamide), and poly (vinylpyrrolidone-co-maleate). The copolymer of vinylpyrrolidone can be added in an amount that is effective to increase the stiffness or elastic modulus (Young's Modulus) of the film relative to a film that does not include copolymer of vinylpyrrolidone and is otherwise the same. Bending stiffness can be determined by applying a measured moment to the film and determining the quotient of the applied moment divided by the resulting curvature of the film. A suitable amount of copolymer of vinylpyrrolidone is from 0.1% to 25% of the weight (or mass) of the film, e.g., 0.2% to 20%, 0.5% to 20%, 1% to 15%, 2% to 15% or 5% to 15%.

Addition of a copolymer of vinylpyrrolidone can advantageously increase stiffness without adversely affecting wettability, disintegration rate or mouth feel by adding titanium dioxide in an amount such that the weight (or mass) ratio of copolymer of vinylpyrrolidone to titanium dioxide in the film is from 3:1 to 5:1. A suitable amount of titanium is, for example, from about 0.02% to about 8%, e.g., 0.04% to about 7%, 0.1% to about 7%, 0.2% to 5%, 0.4% to 5%, or 1% to 5%.

Within the disclosed ranges for the vinylpyrrolidone copolymer and the titanium dioxide, it is possible to achieve an advantageous balance or combination of improved stiffness or higher elastic modulus while concurrently achieving rapid disintegration and good mouth feel.

The titanium dioxide can be added in amounts from about 0.05% to 5%, 0.1% to 3%, or 0.5 to 2% of the weight of the film. The titanium dioxide acts as a disintegrant in the disclosed films, as well as a texture modifier that improves mouth feel, and an opacify or coloring agent. This amount is effective for increasing the rate at which the film will dissolve in an aqueous medium. The amount of copovidone added can be an amount by weight that is from 3 to 5 times the weight of the titanium dioxide. The titanium dioxide provides an increased rate of disintegration relative to an otherwise identical composition that does not contain titanium dioxide. The increased rate of disintegration can be at least 5%, at least 10%, at least 20%, at least 50% or at least 75%.

In certain embodiments, the disclosed films may include a plasticizer. The term "plasticizer" refers to a component that reduces the glass-transition temperature of the film forming polymers (e.g., the water soluble polymer or water soluble polymers in the film). The plasticizer increases the flexibility, enhances elasticity and reduces brittleness of the film. Examples of plasticizers that can be used in the disclosed film oral dosage forms include triacetin, triethyl citrate, tributyl citrate, acetyl tributyl citrate, acetyl triethyl citrate, trioctyl citrate, acetyl trioctyl citrate, trihexyl citrate, dibutyl sebacate, etc. Plasticizer may be added in an amount up to 25% of the total mass of the film oral dosage form, such as from 0.5% to 25%, 1% to 20%, 2% to 15% or 5% to 10%.

The amount of drug that can be incorporated in the film oral dosage forms disclosed herein is generally from 0.01% to 50% by total weight of the film, such as 1% to 40%, 2% to 30%, or 5% to 20% by total weight of the film.

Conventional film oral dosage form additives, other than surfactants and polyalcohols, can be added as needed or desired, generally in amounts conventionally employed. Examples of such additives include artificial sweeteners such as sucralose, aspartame, acesulfame potassium and monoammonium glycyrrhizinate, natural sweeteners such as sucrose and fructose; flavorants such as menthol, various fruit flavors (e.g., cherry, grape, orange, etc.) or various mint flavors (e.g., spearmint, peppermint, etc.); colorants; opacifiers (e.g., titanium dioxide); and antioxidants (e.g., butylhydroxytoluene). Other additives may also be incorporated in amounts that do not adversely affect film properties or film stability. Specifically, any such additives must not cause undesirable softening of the film and subsequent loss of dimensional stability, degradation of the active ingredient(s), or induce undesirable aesthetics such as discoloration of the film or noticeable segregation and agglomeration of film components.

In an embodiment, a method of forming a film of the present disclosure includes combining the various ingredients in generally any order, employing water, a combination of water and water-miscible solvents such as lower alcohols (e.g., ethanol) or organic solvents alone or as a mixture. For example, the plasticizer and additives (e.g., sweetening agents, colorants, flavorants, and opacifying agents) can be dissolved or dispersed in a sufficient amount of solvent that is agitated to form a homogenous solution or suspension to which the water soluble polymer(s) is (are) added. Heat, vacuum and agitation may be applied as needed during addition of the water soluble polymer until a homogenous solution or homogenous suspension is obtained. Thereafter, the active ingredient(s) is (are) added, and the solution or suspension is cast or coated onto a carrier material and dried to form a film. Examples of suitable carrier materials include non-siliconized polyethylene terephthalate film, non-siliconized kraft paper, polyethylene-impregnated kraft paper and non-siliconized polyethylene film. The liquid film composition can be coated onto the carrier material using generally any conventional coating equipment, including knife-over-roll, extrusion die, reverse roll, or Meyer roll coating equipment.

Upon drying, the resulting solid film can have a thickness of generally 5 to 200 µm, such as 10 to 200 µm, 20 to 150 µm or 20 to 100 µm. The film can be cut into individual pieces having a suitable size to facilitate administration of a targeted dosage of active agent(s).

EXAMPLE 1

Rizatriptan film oral dosage forms are prepared using the above described processes and compositions listed in the following Table 1.

TABLE 1

| Component | Function | Quantity per dry film [mg] 2.58 cm$^2$ | Quantity per dry film [mg] 5.16 cm$^2$ | Quantity per dry film [%] |
|---|---|---|---|---|
| Hydroxymethyl ethyl cellulose | Film forming polymer | 6.2 mg | 12.400 mg | 15.39 |
| Copovidone | Film forming polymer | 2.0 mg | 4.0 mg | 4.96 |
| Hydroxypropylmethyl cellulose | Film forming polymer | 20.203 mg | 40.405 mg | 50.14 |
| Butylhydroxyltoluene | antioxidant | 0.004 mg | 0.008 mg | 0.010 |
| Monoammonium Glycyrrhizinate | sweetener | 0.222 mg | 0.443 mg | 0.550 |
| Sucralose | sweetener | 0.439 mg | 0.878 mg | 1.090 |
| Titanium dioxide | Opacifier/texture modifier | 0.661 mg | 1.322 mg | 1.640 |
| Menthol | flavour | 0.439 mg | 0.878 mg | 1.090 |
| Dibutyl sebacate | plasticizer | 2.861 mg | 5.722 mg | 7.100 |
| Rizatriptan benzoate | active | 7.265 mg | 14.530 mg | 18.030 |
| Total | | 40.294 mg | 80.586 mg | 100.000 |

The resulting rizatriptan films were stable for at least 18 months at 25° C. and 65% relative humidity and for at least 6 months at 40° C. and 75% relative humidity. Subjective testing, in which the subject was asked to moisten her mouth with a small amount of water and swallow the water before the film was placed on the tongue and the mouth was closed, indicated that the films had good mouth feel (i.e., was not unpleasant) and dissolved completely within a short period, typically within less than 15 minutes, less than 10 minutes, less than 5 minutes, less than 2 minutes, or even less than 1 minute. The subjects were advised that the film should not be chewed or swallowed but allowed to dissolve in available saliva. The time for disintegration is recorded as the time the film takes to completely disappear.

EXAMPLE 2

Palonosetron (a 5-HT$_3$ antagonist used to prevent or treat chemotherapy-induced nausea and vomiting) film oral dosage forms are prepared using the above described processes and compositions listed in the following Table 2.

TABLE 2

| Component and Quality Standard (and Grade, if applicable) | Function | Quantity per dry film [mg] | Quantity per dry film [%] |
|---|---|---|---|
| Palonosetron | active | 2.50 | 4.77 |
| L-Cysteine | anti-oxidant | 0.34 | 0.65 |
| Sucralose | sweetener | 0.52 | 0.99 |

TABLE 2-continued

| Component and Quality Standard (and Grade, if applicable) | Function | Quantity per dry film [mg] | Quantity per dry film [%] |
|---|---|---|---|
| Hydroxypropyl cellulose | Film forming polymer | 23.10 | 44.12 |
| Copovidone | Film forming polymer | 2.5 mg | 4.77 |
| Hydroxypropylmethyl cellulose | Film forming polymer | 15.02 | 28.69 |
| Titanium dioxide | Opacifier/texture modifier | 0.52 | 0.99 |
| Polyvinyl pyrrolidone | Film forming polymer | 6.72 | 12.83 |
| Anhydrous citric acid | acidifier | 1.14 | 2.18 |
| Total | | 52.36 mg | 100.0 |

EXAMPLE 3

Alprazolam film oral dosage forms are prepared using the above described processes and compositions listed in the following Table 3.

TABLE 3

| Component and Quality Standard (and Grade, if applicable) | Function | Quantity per dry film [mg] | Quantity per dry film [%] |
|---|---|---|---|
| Alprazolam | active | 2.00 | 4.68 |
| Acesulfame potassium | sweetener | 0.39 | 0.91 |
| Copovidone | Film forming polymer | 8.75 | 20.51 |
| Hydroxypropyl cellulose | Film forming polymer | 27.62 | 64.74 |
| Triethyl citrate | Plasticzer | 1.58 | 3.70 |
| Titatnium dioxide | Opacifier/texture modifier | 1.75 | 4.10 |
| Menthol | Flavour | 0.55 | 1.29 |
| Yellow #6 | Colour | 0.02 | 0.05 |
| Total | | 42.66 mg | 100.0 |

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. An instantly wettable, rapidly disintegrating film oral dosage form, comprising:
   at least one water soluble polymer that is not a copolymer of vinylpyrrolidone;
   at least one copolymer of vinylpyrrolidone in an amount that is effective to increase stiffness of the film as compared to a film without the at least one copolymer of vinylpyrrolidone;
   titanium dioxide in an amount that is effective to increase a rate of disintegration of the film in an aqueous medium, wherein the ratio by weight of copolymer of vinylpyrrolidone to titanium dioxide in the film is from 3:1 to 5:1; and
   at least one active agent;
   wherein the film oral dosage form is substantially free of surfactants and polyalcohols.

2. The oral dosage form of claim 1, further comprising a plasticizer.

3. The oral dosage form of claim 1, further comprising a synthetic sweetener.

4. The oral dosage form of claim 1, further comprising a natural sweetener.

5. The oral dosage form of claim 1, further comprising a flavorant.

6. The oral dosage form of claim 1, further comprising an antioxidant.

7. The oral dosage form of claim 1, in which the at least one water soluble polymer that is not a copolymer of vinylpyrrolidone includes hydroxypropyl cellulose.

8. The oral dosage form of claim 1, in which the at least one water soluble polymer that is not a copolymer of vinylpyrrolidone includes a combination of hydroxypropyl cellulose and polyvinylpyrrolidone.

9. The oral dosage form of claim 1, in which the active agent is selected from the group consisting of rizatriptan, zolmitriptan, alprazolam, diazepam or lorazepam.

10. The oral dosage form of claim 1, in which the active agent is rizatriptan benzoate.

11. The oral dosage form of claim 1, in which the at least one water soluble polymer that is not a copolymer of vinylpyrrolidone consists of a combination of hydroxypropyl cellulose and polyvinylpyrrolidone and further comprising a plasticizer.

12. The oral dosage form of claim 1 further comprising at least one plasticizer and at least one additive selected from the group consisting of synthetic sweeteners, natural sweeteners, flavorants, antioxidants, colorants, and opacifiers.

13. An instantly wettable, rapidly disintegrating film dosage form comprising at least one water soluble polymer that is not a copolymer of vinylpyrrolidone, at least one copolymer of vinylpyrrolidone, at least one active agent, at least one plasticizer, titanium dioxide in an amount that is effective to increase a rate of disintegration of the film in an aqueous medium, wherein the ratio by weight of copolymer of vinylpyrrolidone to titanium dioxide in the film is from 3:1 to 5:1, and optional additives.

14. The oral dosage form of claim 13, in which the plasticizer is triacetin.

15. The oral dosage form of claim 13, in which the at least one water soluble polymer includes hydroxypropyl cellulose.

16. The oral dosage form of claim 13, in which the at least one water soluble polymer consists of a combination of hydroxypropyl cellulose and polyvinylpyrrolidone.

17. The oral dosage form of claim 13, in which the at least one active agent is rizatriptan or rizatriptan benzoate.

18. An instantly wettable, rapidly disintegrating film dosage form consisting of hydroxypropyl cellulose, polyvinylpyrrolidone, triacetin, vinylpyrrolidone-vinyl acetate copolymer, titanium dioxide, and at least one active agent, wherein the ratio of vinylpyrrolidone-vinyl acetate copolymer to titanium dioxide is from 3:1 to 5:1.

19. The oral dosage form of claim 18, in which the at least one active agent is rizatriptan benzoate.

20. An instantly wettable, rapidly disintegrating film oral dosage form, comprising:
   at least one of a water soluble cellulose derivative and polyvinyl pyrrolidone;

at least one copolymer of vinylpyrrolidone in an amount that is effective to increase stiffness of the film as compared to a film without the at least one copolymer of vinylpyrrolidone;
titanium dioxide in an amount wherein the ratio of weight of copolymer of vinylpyrrolidone to titanium dioxide in the film is from 3:1 to 5:1; and
at least one active agent;
wherein the film oral dosage form is substantially free of surfactants and polyalcohols.

* * * * *